US009656103B2

(12) United States Patent
Müller et al.

(10) Patent No.: US 9,656,103 B2
(45) Date of Patent: May 23, 2017

(54) LIGHT PROTECTING-EFFECTIVE COSMETIC OR DERMATOLOGICAL PREPARATIONS

(75) Inventors: Stefan Müller, Weil am Rhein (DE); Thomas Ehlis, Freiburg (DE); Jochen Giesinger, Grenzach-Wyhlen (DE); Gilbert Kreyer, Saint-Louis (FR)

(73) Assignee: BASF SE, Ludwigshafen (DE)

( * ) Notice: Subject to any disclaimer, the term of this patent is extended or adjusted under 35 U.S.C. 154(b) by 1467 days.

(21) Appl. No.: 11/632,686

(22) PCT Filed: Jul. 11, 2005

(86) PCT No.: PCT/EP2005/053301
§ 371 (c)(1),
(2), (4) Date: Aug. 30, 2007

(87) PCT Pub. No.: WO2006/008252
PCT Pub. Date: Jan. 26, 2006

(65) Prior Publication Data
US 2008/0075746 A1    Mar. 27, 2008

(30) Foreign Application Priority Data

Jul. 20, 2004 (EP) .................................. 04103462
Oct. 14, 2004 (EP) .................................. 04105034

(51) Int. Cl.
| A61Q 17/04 | (2006.01) |
| A61K 8/02 | (2006.01) |
| A61K 9/107 | (2006.01) |
| A61K 8/06 | (2006.01) |

(52) U.S. Cl.
CPC ............... *A61Q 17/04* (2013.01); *A61K 8/02* (2013.01); *A61K 9/107* (2013.01); *A61K 2800/412* (2013.01)

(58) Field of Classification Search
CPC .......... A61K 8/29; A61K 8/42; A61K 8/4946; A61K 8/496; A61K 8/4966; A61K 8/73; A61K 8/8147; A61K 8/8176; A61K 8/0241; A61K 8/0279; A61K 2800/412; A61K 2800/652; A61K 2800/654; A61Q 17/04; Y10S 514/937
See application file for complete search history.

(56) References Cited

U.S. PATENT DOCUMENTS

| 3,988,437 | A | * | 10/1976 | Bradner ........................ 424/59 |
| 4,800,076 | A | * | 1/1989 | Bhat et al. ..................... 424/69 |
| 5,486,233 | A | * | 1/1996 | Mitchell et al. ............. 106/416 |
| 5,733,531 | A | | 3/1998 | Mitchnick et al. ............ 424/59 |
| 5,853,705 | A | * | 12/1998 | Nakayama et al. ........... 424/59 |
| 5,869,030 | A | * | 2/1999 | Dumler et al. ................. 424/59 |
| 6,007,799 | A | * | 12/1999 | Lee et al. ....................... 424/65 |
| 6,015,548 | A | * | 1/2000 | Siddiqui et al. ............... 424/59 |
| 6,159,481 | A | * | 12/2000 | Fallick ......................... 424/401 |
| 6,210,658 | B1 | * | 4/2001 | Bonda ............................ 424/59 |
| 6,235,271 | B1 | | 5/2001 | Luther et al. ................... 424/59 |
| 6,294,143 | B1 | * | 9/2001 | Deutsch et al. ............. 423/432 |
| 6,355,230 | B2 | * | 3/2002 | Gers-Barlag et al. ......... 424/59 |
| 6,485,713 | B1 | * | 11/2002 | Bonda et al. .................. 424/59 |
| 6,495,122 | B2 | | 12/2002 | Fankhauser et al. .......... 424/59 |
| 6,511,655 | B1 | * | 1/2003 | Muller et al. .................. 424/59 |
| 6,627,179 | B2 | * | 9/2003 | Candau ......................... 424/59 |
| 6,746,666 | B1 | * | 6/2004 | Luther .......................... 424/59 |
| 2003/0082464 | A1 | * | 5/2003 | Takashima et al. ............ 430/7 |
| 2003/0124048 | A1 | * | 7/2003 | Hardinghaus et al. ...... 423/554 |
| 2003/0161894 | A1 | * | 8/2003 | Yaniv .......................... 424/687 |
| 2004/0081633 | A1 | * | 4/2004 | Mercier et al. ........... 424/70.12 |
| 2005/0008665 | A1 | * | 1/2005 | Batzer et al. ................ 424/401 |
| 2005/0196360 | A1 | | 9/2005 | Comte et al. .................. 424/59 |
| 2006/0058430 | A1 | * | 3/2006 | Dyllick-Brenzinger et al. .......................... 524/115 |

FOREIGN PATENT DOCUMENTS

| EP | 0 893 119 | 1/1999 |
| EP | 1 068 866 | 1/2001 |
| EP | 1308154 A2 | * 5/2003 |
| JP | 60149517 A | * 8/1985 |
| NL | WO 2004110614 A1 | * 12/2004 ............. B01J 13/06 |
| WO | 00/78277 | 12/2000 |
| WO | WO 0200190 A1 | * 1/2002 |
| WO | 03/063814 | 8/2003 |

OTHER PUBLICATIONS

Gerhard J. Nohynek and Hand Schaefer, Benefit and Risk of Organic Ultraviolet Filters, Regulatory Toxicology and Pharmacology 33, 285-299 (2001).*
Federal Register vol. 64, No. 98, p. 27666 (1999).*
Dolomite Product information and Date; available at http://www.mindat.org/min-1304.htm.*
Dolomite Powder; available at http://www.steatiteindia.com/dolomite.htm.*
Wetting behavior of magnesite and dolomite surfaces; , Applied Surface Science; vol. 252, Issue 10, p. 3744-3750; available online Jul. 5, 2005.*
Melamine Fact Sheet from Fisheries Perspective (2008). Available at: www.globefish.org/filedownload.php?fileld=690.*
2,4,6-triphenyl-1,3,5-triazine MSDS.*
Weber, Handbook of Optical Materials, CRC Press (2003) Table 1.3.3.*

(Continued)

*Primary Examiner* — Kortney L Klinkel
*Assistant Examiner* — Lisbeth C Robinson
(74) *Attorney, Agent, or Firm* — Marshall, Gerstein & Borun LLP

(57) ABSTRACT

Disclosed is the use of an insoluble or sparingly soluble micronized substance class which is not a cosmetic UV absorber and which is dispersed in the oil- or water-phase of a cosmetic or dermatological composition for the enhancement of light protecting action of this cosmetic or dermatological composition comprising at least one cosmetic UV filter which is soluble in the water- or oil-phase. The cosmetic preparation according to the invention shows a remarkable increase in SPF.

12 Claims, No Drawings

(56) References Cited

OTHER PUBLICATIONS

Wypych, "Barium Sulfate", Handbook of Fillers, ChemTec Publishing, Toronto (2010) pp. 31-35.*
Bala et al., Colloids and Surfaces A, 274: 71-76 (2006).*
Mizuguchi et al. JP, 60-0149517, English language Abstract (1985).*
Mizuguchi et al. JP, 60-0149517, Derwent Abstract 1985-2342456 (1985).*
Ultraviolet. The American Heritage Dictionary (2007). Retrieved from http://www.credoreference.com/entry/hmmedicaldict/ultraviolet, Dec. 5, 2012.*
Derwent Abstract 1992-344665 for JP, 4-248877 (1992).*
Baudour et al., Acta Crystal., B34: 625 (1978) (Abstract).*
pTerphenyl MSDS, accessed at http://www.sciencelab.com/msds.php?msdsId=9925178, May 23, 2013.*
Hawley's, Hawley's Condensed Chemical Dictionary, Lewis, eds. Wiley & Sons, Inc. New York, (2007) p. 1067.*
Machine Translation of EP1308154, Google Patents, downloaded Jan. 9, 2014.*
Machel et al., Luminescence Microscopy and Spectroscopy (1991) pp. 1-2 (submitted by Applicant).*
Hassan, American Mineralogist, 63: 732-736 (1978).*
English Language Abstract for EP 1 068 866 printed from esp@cenet.com on Apr. 30, 2007.
UV Spectrum Melamine; Journal of Chromatography A; vol. 815; Issue 2; Jul. 31, 1998; pp. 197-204.
Reaxys ID #45961; N-N-N-triphenynl-triazine.
Reaxys ID #293951; 2-4-6-tris-methyl-phenyl-triazine.*
Reaxys ID #239186; 2-4-6-triphenyl-triazine.

* cited by examiner

LIGHT PROTECTING-EFFECTIVE COSMETIC OR DERMATOLOGICAL PREPARATIONS

The present invention relates to the use of specific micronized insoluble substances for the enhancement of light protecting action in cosmetic or dermatological compositions and cosmetic or dermatological compositions comprising these specific micronized insoluble substances.

It is well known that specific organic UV filters, like sparingly soluble benzotriazoles or triazine compounds exhibit pronounced UV filter properties and are therefore used in cosmetic UV filter compositions.

A problem of these organic UV filters is their low solubility in cosmetic oils. Their use in oil phase containing cosmetic formulations is therefore limited to only low concentration levels.

Micronized organic UV filters are generally used as aqueous dispersions and can therefore only be formulated in the water phase.

Surprisingly it was found that dispersions of micronized insoluble substances are able to enhance the light protecting action of a cosmetic or dermatological composition comprising an organic UV filter which is dissolved in the oil- or water-phase of this composition.

Therefore, the present invention relates to the use of an insoluble or sparingly soluble micronized substance class which is not a cosmetic UV absorber and which is dispersed in the oil- or water-phase of a cosmetic or dermatological composition for the enhancement of light protecting action of this cosmetic or dermatological composition comprising at least one cosmetic UV filter which is soluble in the water- or oil-phase.

The micronized insoluble substance class is preferably a birefringent substance having an average refraction index of n=1 to 2.5 and a Δn=0.001 to 0.8 n.

"Birefringent" substances are understood as non-absorbing materials, wherein the pass of electromagnetic radiation is dependent on the propagation direction of the light (=optical anisotropy).

If the overall light ray is regarded as two perpendicular linear polarized light rays the velocity of propagation and consequently the refraction index is different for both rays.

Preferably the micronized insoluble or sparingly soluble substances have a hydrophobic or hydrophilic surface.

Preferably they are present in the composition in crystalline or in part crystalline form.

Preferably the micronized insoluble or sparingly soluble substance has a high melting point, which is normally >80° C., more preferably >100° C., and most preferably >120° C.

Most preferably substances are used which have an aromatic or heteroaromatic moiety.

Examples for micronized insoluble substances having an aromatic or heteroaromatic moiety are:

Triazine derivatives, like melamine, 2,4,6-triamino-s-triazin; melamine polyphosphate (CAS Regno. 218768-84-4); melamine cyanurate (CAS Regno. 37640-57-6); melamine phosphate (CAS Regno. 41583-09-9); melam, (1,3,5-triazine-2,4,6-triamine-n-(4,6-diamino-1,3,5-triazine-2-yl) of the formula

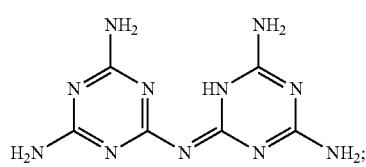 [SMILES: Nc1nc(N)nc(/N=c2/nc(N)nc(N)[nH]2)n1]

melem, (-2,5,8-triamino 1,3,4,6,7,9,9b-heptaazaphenalene) [1502-47-2] of the formula

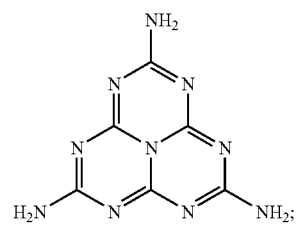

melon, (poly [8-amino-1,3,4,6,7,9,9b-heptaazaphenalene-2,5-diyl)imino] of the formula

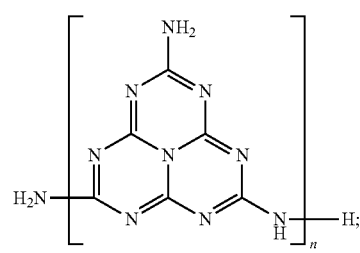

1,3,5-triazin-2(1H)-one, 4,6-diamino-, (Registry Number: 645-92-1) of the formula

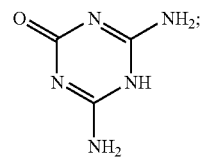

1,3,5-triazine-2,4(1 H,3H)-dione, 6-amino-(Registry Number: 645-93-2) of the formula

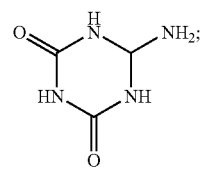

aryl-triazines and arylamino-triazines of the formulae

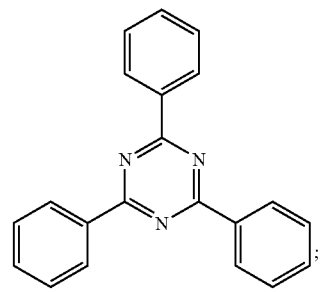

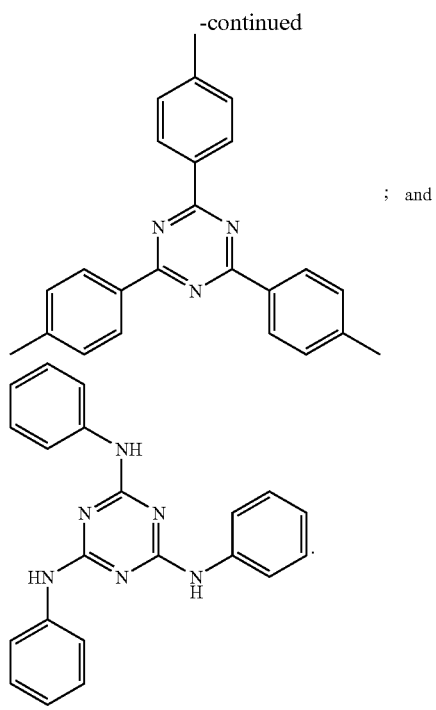

Furthermore, the following organic micronized substances are suitable for the present invention:
Amides, like benzene-1,2,4,5-tetracarboxamide, biphenyl-4,4'-dicarboxamide, biphenyl-4-carboxylic amide, isophthalamide and terephthalamide;
Urea derivatives, like cyanuric acid, diphenyl urea, propoylurea and 3-methyl-1,1-di-phenylurea;
Isatin;
5-amino-isophthalic acid;
phenyl compounds, like diphenyl sulfone, p-quaterphenyl or p-terphenyl; and
the triazine compound of formula

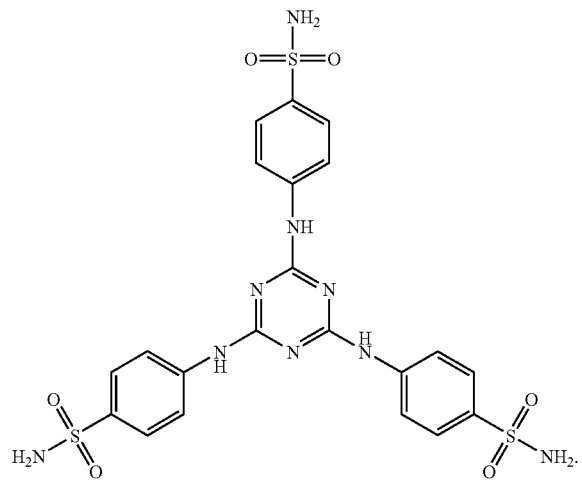 [SMILES: NS(=O)(=O)c1ccc(Nc2nc(Nc3ccc(S(N)(=O)=O)cc3)nc(Nc3ccc(S(N)(=O)=O)cc3)n2)cc1]

Furthermore, micronized, insoluble substances are useful for the present invention which have mineral character, like the following metal salts:
Aluminum salts, like aluminum hydroxide $Al(OH)_3$ and aluminum phosphate $AlPO_4$;
Barium salts, like barium carbonate $BaCO_3$, barium chromate $BaCrO_4$, barium fluoride $BaF_2$, barium hydroxide $Ba(OH)_2$, barium sulfate $BaSO_4$, barium sulfite $BaSO_3$, barium thiosulfate $BaS_2O_3$;
Bismut salts like bismuthyl chloride BiOCl and bismuthyl hydroxide BiOOH;
Cadmium salts like cadmium carbonate $CdCO_3$, cadmium hydroxide $Cd(OH)_2$, cadmium oxalate $CdC_2O_4$ and cadmium sulfide* CdS;
Calcium slats, like calcium carbonate $CaCO_3$ (Calcit), calcium magnesium carbonate (dolomite), calcium chromate $CaCrO_4$, calcium fluoride $CaF_2$, calcium hydrogen phosphate $CaHPO_4$, calcium hydroxide $Ca(OH)_2$, calcium oxalate $CaC_2O_4$, calcium phosphate $Ca_3PO_4$, calcium sulfate $CaSO_4$ and calcium sulfite $CaSO_3$;

Calcium carbonate [471-34-1] occurs naturally as chalk, limestone, and marble. It can be used according to the present invention.

Preferably used in the present invention are ground calcium carbonate (GCC), fine-ground calcium carbonate (FGCC) andultrafine ground calcium carbonate which are often referred to as natural carbonate.

Calcium carbonate has three polymorphic forms: calcite (rhombohedral), aragonite (orthorhombic), and vaterite (trigonal). All three forms are preferably used in the present invention. Most preferably used is calcite.

Preferably used in the present invention are also calcium carbonates which are produced chemically by precipitation (precipitated calcium carbonate, PCC). They are characterized by greater particle fineness. There are many PCC morphologies possible that are based on rhombohedral, prismatic, scalenohedral and also spherical and needlelike crystal structures. Examples are Rhombohedral (PCC-R) or barrel-shaped calcium carbonate particles, Prismatic PCC calcium carbonate particles, Scalenohedral (PCC-S) or rosette-shaped calcium carbonate particles.

Dolomite is alyo preferably used in the present invention. The typical physical properties of Calcium Carbonates are listed in the Table below:

| Typical physical properties of Calcium Carbonates | GCC/PCC | Dolomite |
| --- | --- | --- |
| molecular weight (Dalton) | 100.09 | 184.4 |
| density (kg l$^{-1}$) | 2.71 | 2.87 |
| Mohs' hardness | 3 | — |
| decomposition T° (K) | from 1150 | from 675 |
| solubility at 288° K (kg l$^{-1}$) | 14 10$^{-6}$ | 320 10$^{-6}$ |
| thermal conductivity (WK$^{-1}$ m$^{-1}$) | 2.4-3.0 | 5-9 |
| specific heat (kJ kg$^{-1}$ K$^{-1}$) | 0.86 | 0.9 |
| linear coefficient of expansion (K$^{-1}$) | 9 10$^{-6}$ | 15 10$^{-6}$ |
| mean refractive index | 1.59 | 1.60 |
| birefringence indices | 1.480-1.650 | 1.500-1.679 |
| % brightness (DIN 1053163) (%) | 88-96 | 88-95 |
| dielectric constant | 6.1 | 7.3 |

Appropriate forms of (precipitated) calcium carbonates are described for instance in: Microemulsion-based synthesis of stacked calcium carbonate (calcite) superstructures. Viravaidya, Chulanapa; Li, Mei; Mann, Stephen. School of Chemistry, University of Bristol, Bristol, Chemical Communications (Cambridge, United Kingdom) (2004), (19), 2182-2183; Tong, Zhongliang. Production situation of nano-calcium carbonate and its application process in China. Huagong Jinzhan (2003), 22(4), 372-375; Ma, Jing; Li, Qingshan; Yang, Zhanguo; Li, Chao; Zhang, Weixing. Manufacture and application of nano calcium carbonate.

Huagong Shikan (2002), 16(7), 11-13; Hu, Qingfu; Hu, Xiaobo; Liu, Baoshu. New retrofitted spraying carbonation technology for preparation of nanometer grade calcium carbonate. Feijinshukuang (2002), 25(4), 42-44, 21; Kato, Takashi; Yabuuchi, Kazuhiro; Sugawara, Ayae; Kishimoto, Kenji. Self-assembly of nano- and micro-structured functional materials. Materia (2003), 42(6), 453-456; Colfen, Helmut. Precipitation of carbonates: recent progress in controlled production of complex shapes. Current Opinion in Colloid & Interface Science (2003), 8(1), 23-31; Sugihara, Hisao. Regulation of morphology of calcium carbonate. Nippon Setchaku Gakkaishi (2003), 39(4), 157-162; Onoe, Kaoru; Matsumoto, Masakazu; Shikata, Yohei; Furukawa, Yuko. Reactive crystallization of calcium carbonate from view point of equilibrium theory of multicomponent aqueous solution; Journal of the Society of Inorganic Materials, Japan (2003), 10(302), 3-11; Berdonosov, S. S.; Berdonosova, D. G.; Znamenskaya, I. V. Industrial synthesis, properties, and use of ultrafine calcium carbonate. Khimicheskaya Tekhnologiya (Moscow, Russian Federation) (2002), (8), 2-11.; Korenaga, Takashi. Changes of the manufacturing technique of calcium carbonate and its applications. Journal of the Society of Inorganic Materials, Japan (2002), 9(300), 346-352; Ji, Hongwei; Xu, Huan; Xin, Huizhen; Xia, Ning. Industrial synthesis and application of nano-Calcium carbonate. Qingdao Haiyang Daxue Xuebao (2002), 32(4), 634-640; Qian, Jun-min; Jin, Zhi-hao. New progress in preparation of filler CaCO3 and control of its shape and crystal types. Huagong Kuangwu Yu Jiagong (2002), 31(4), 1-4, 10; Zhao, Chun-xia; Man, Rui-lin; Yu, Jia-geng. Preparation and application of nanometer light calcium carbonate. Yingyong Huagong (2002), 31(2), 4-6; Jiang, Luhua; Du, Fanglin; Zhang, Zhikun; Cui, Zuolin. Preparation and application of ultra-fine calcium carbonate. Zhongguo Fenti Jishu (2002), 8(1), 28-32; Qian, Haiyan; Wang, Yaqin; Ye, Xuchu; Bi, Yunhua. Production and application of ultrafine ground calcium carbonate in China. Feijinshukuang (2001), 24(6), 8-9, 19; Chikazawa, Masatoshi; Fuji, Masayoshi. Nanoparticles of lime and calcium carbonate. Journal of the Society of Inorganic Materials, Japan (2001), 295 507-514; Zhu, Yingquan; Cao, Jianlin; Wang, Chengzhen; Xi, Shaohua; Tan, Jianhua. Quality of high purity CaCO3 made in China and Japan. Dianzi Yuanjian Yu Cailiao (2001), 20(4), 27-29; Han, Xiushan. Production and application of nano CaCO3. Huagong Shikan (2001), 15(5), 51-53; Xiao, Pindong. Factors affecting shape and size of superfine CaCO3 powder prepared by carbonation. Wujiyan Gongye (2001), 33(3), 28-30; Hu, Xiaobo; Liu, Baoshu; Hu, Qingfu. Advances in ground CaCO3. Zhongguo Fenti Jishu (2001), 7(1), 24-28; Hu, Qingfu; Hu, Xiaobo; Liu, Baoshu. Production of superfine ground CaCO3. Feijinshukuang (2001), 24(1), 23-25. CODEN: FEIJDJ ISSN:0253-2298; Wu, Zhijian; Lin, Yanxin; Huang, Liyao. Synthesis of inorganic non-metal films on organic substrates. Gongneng Cailiao (2000), 31(6), 587-589; Hirasawa, lzumi. Formation of calcium carbonate by reaction crystallization. Journal of the Society of Inorganic Materials, Japan (2000), 287 307-312; Imppola, Olavi. Precipitated calcium carbonate—PCC. Papermaking Science and Technology (2000), 11 140-151; Huggenberger, Ludwig; Arnold, Manfred; Koster, Hans-Heinz. Ground calcium carbonate. Papermaking Science and Technology (2000), 11 94-105; Hu, Qingfu; Hu, Xiaobo; Liu, Baoshu. Preparation methods and application of nanometer calcium carbonate. Feijinshukuang (2000), 23(4), 24-26, 12; Ji, Guangbin; Chai, Xiaoli; Chen, Weizhong. Application and preparative process of ultra-fine ground CaCO3. Shanghai Huagong (2000), 25(11), 19-20, 29; Hu, Qingfu; Zhao, Fengqing; Liu, Baoshu; He, Fenglin; Xu, Zhao. Economical scale of production of basic magnesium carbonate, light magnesia, and superfine magnesium-containing calcium carbonate from dolomite by carbonization. Wujiyan Gongye (1999), 31(6), 21-22, 39; Ueyama, Norikazu. Strong binding of polymer ligand to calcium carbonate. Kobunshi (1999), 48(4), 262; Ukai, Kenji; Toyokura, Ken. Reactive crystallization of calcium carbonate. Nippon Kaisui Gakkaishi (1998), 52(5), 292-298; Brown, Alan J. Ground calcium carbonate fillers. Retention of Fines and Fillers during Papermaking (1998), 271-279; Zhang, Shicheng; Zhuge, Lanjian; Han, Yaoxin; Jiang, Junhua. Preparation and application of calcium carbonate with nanometer particle size. Feijinshukuang (1997), (4), 22-25; Prescott, P. I.; Pruett, R. J. Ground calcium carbonate: ore mineralogy, processing and markets. Transactions of Society for Mining, Metallurgy, and Exploration, Inc. (1997), Volume Date 1996, 300 79-84; Ikegami, Tsukasa. Calcium carbonate filler. Kogyo Zairyo (1996), 44(10), 36-37; Chen, Ching Chih; Chen, Chih Hsien. High-purity calcium carbonate powders. Kuangye (Taipei, Taiwan) (1991), 35(4), 75-87; Nukui, Tokuzo. Development of calcium carbonate fillers. Gypsum & Lime (1990), 228 303-9; Hu, Zhitong. New types of calcium carbonate. Huaxue Shijie (1986), 27(3), 99-101; Ikegami, Tsukasa. History of calcium carbonate powder. Toso Kogaku (1981), 16(6), 224-8; Kamiya, Kanichi; Sakka, Sumio. Formation of calcium carbonate polymorphs. Gypsum & Lime (1979), 163 243-53.

Coated or surface modified calcium carbonate can be used according to the present invention. Surface treatment methods and appropriate materials are described in:

| | |
|---|---|
| JP 54107929 | Surface treatment of calcium carbonate for solvent-type coating compositions. |
| JP 62148572 | Pigments for coated paper |
| JP 01090235 | Polyolefin resin compositions and laminated products of metals and resin composition layers. |
| JP 04004075 | Process for coating fillers with surface modifiers. |
| JP 04006105 | Surface treatment of calcium carbonate for improvement of its dispersibility. |
| JP 08231760 | Surface-treated, heavy calcium carbonate and its use in vinyl chloride-based polymer compositions |
| JP 11349846 | Surface treatment of calcium carbonate filler. |
| JP 2001072890 | Surface-treated calcium carbonate, their thermoplastic resin compositions, and manufacture of porous films from the compositions. |
| JP 2001288371 | Antibacterial polymer compositions containing surface-treated inorganic fillers and their manufacture. |
| JP 2003034760 | Surface-treated heavy calcium carbonate with good dispersibility, their manufacture, and resin compositions containing them. |
| Zhang, Yi; Ma, Xiuqing; Jin, Riguang; Tian, Miao. Beijing University of Chemical Technology, Beijing, Peop. Rep. China. Suliao (2003), 32(3), 59-64. | Surface treatment of nano CaCO3 and its composite with polymers |

According to the present invention acid resistant calcium carbonate can be used. The following references describe appropriate forms of modified calcium carbonate:

WO 2003075874; Guo, Fen; Wu, Hai-xia; Chen, Jianfeng; Liu, Run-jing; Wang, Dong-guang: "Preparation of acid-resistant calcium carbonate" Huagong Kuangwu Yu Jiagong (2003), 32(5), 5-7, 23; WO 9902608; WO 9856860; WO 9820079; WO 9714847; WO 9714651; U.S. Pat. Nos.

5,593,489 A; 5,593,488 A; Patel, M.; Panigrahi, J. C.: "Acid resistant calcium carbonate for sizing in paper manufacturing", Journal of Scientific & Industrial Research (1996), 55(11),879-884; U.S. Pat. Nos. 5531821 A; 5,164,006 A; AND DE-A-2059624

Instead of calcium carbonate kaolins [14808-70-7], [14808-60-7], [1332-58-7] or natural calcium or magnesium silicates can be used. These products occur naturally as talc [14807-96-6], or wollastonite Instead of calcium carbonate, crystalline silicon dioxide can be used.

Silicon dioxide occurs naturally in both the crystalline and the amorphous forms. Crystalline silicon dioxide is used mostly in the form of ground quartz. Neuburger Kieselerde (trade name sillitin) has a particular structure. It consists of corpuscular quartz [14808-60-7] and laminar kaolinit [1318-74-7].

- Chromium salts, like chromium(II) hydroxide $Cr(OH)_2$ and chromium(III) hydroxide $Cr(OH)_3$;
- Cobalt salts like cobalt(II) carbonate $CoCO_3$; cobalt(II) hydroxide $Co(OH)_2$, cobalt(III) hydroxide $Co(OH)_3$ and cobalt(II) sulfide $CoS$;
- Copper salts like copper(I) chloride $CuCl$, copper(I) iodide $CuI$, copper(II) carbonate $CuCO_3$, copper(II) ferrocyanide $Cu[Fe(CN)6]$, copper(II) hydroxide $Cu(OH)_2$ and copper(II) sulfide $CuS$;
- Iron salts, like iron(II) carbonate $FeCO_3$, iron(II) hydroxide $Fe(OH)_2$, iron(II) sulfide Fees, iron(III) ferrocyanide $Fe_4[Fe(CN)6]_3$; iron(II) hydroxide $Fe(OH)_3$ and iron(III) phosphate $FePO_4$;
- Lead salts, like lead(II) fluoride $PbF_2$, lead(II) hydroxide $Pb(OH)_2$, lead(II) iodide $PbI_2$, lead(II) sulfate $PbSO_4$, and lead(II) sulfide $PbS$;
- Lithium salts, like lithium carbonate $Li_2CO_3$, lithium fluoride $LiF$ and lithium phosphate $Li_3PO_4$;
- Magnesium salts, like magnesium ammonium phosphate $MgNH_4PO_4$, magnesium carbonate $MgCO_3$, magnesium fluoride $MgF_2$, magnesium hydroxide $Mg(OH)_2$, magnesium oxalate $MgC_2O_4$ and magnesium phosphate $Mg_3PO_4$;
- Manganese salts, like manganese(II) carbonate $MnCO_3$, manganese(II) hydroxide $Mn(OH)_2$ and manganese(II) sulfide $MnS$;
- Nickel salts, like nickel(II) hydroxide $Ni(OH)_2$ and nickel (II) sulfide $NiS$;
- Silver salts, like silver sulfate $Ag_2SO_4$, silver sulfide $Ag_2S$, silver sulfite $Ag_2SO_3$ and silver thiocyanate $AgSCN$;
- Strontium salts, like strontium carbonate $SrCO_3$, strontium fluoride $SrF_2$ and strontium sulfate $SrSO_4$;
- Thallium salts like thallium(III) hydroxide $Tl(OH)_3$;
- Tin salts, like tin(II) hydroxide and tin(II) sulfide $SnS$;
- Zinc salts like $Sn(OH)_2$; zinc carbonate $ZnCO_3$; zinc hydroxide $Zn(OH)_2$; zinc oxalate $ZnC_2O_4$; zinc phosphate $Zn_3PO_4$; and zinc sulfide $ZnS$.

Furthermore, clay minerals are preferably used as micronized substances in the present invention.

Preferred are
(I) Amorphous Allophane group, and
(II) crystalline clay minerals, which may be categorized into
   (A) two-layer types (sheet structures composed of units of one layer of silica tetrahedrons and one layer of alumina octahedrons), for example equidimensional kaolin group, kaolinite, dickite and nacrite and elongate halloysite;
   (B) three-layer types (sheet structures composed of two layers of silica tetrahedrons and one central dioctahedral or trioctahedral layer); for example expanding lattice Smectite group (equidimensional montmorillonite, sauconite, vermiculite, elongate nontronite, saponite and hectorite) and nonexpanding lattice, Illite group;
   (C) regular mixed-layer types (ordered stacking of alternate layers of different types, Chlorite group); and
   (D) chain-structure types (hornblende-like chains of silica tetrahedrons linked together by octahedral groups of oxygens and hydroxyls containing aluminum and magnesium ions), hormite group palygorskite, (attapulgite) and sepolite.

Furthermore, silica and layered silica, preferably microcrystalline silica minerals are preferably used as micronized inorganic, insoluble substances.

Examples and properties of these materials are listed in the table below:

| Mineral or phase | Species | Microstructure |
|---|---|---|
| Quartz | microquartz | granular grains <20 μm |
|  | chalcedony | length fast fibers, fiber axis <11.0> parallel fibrous spherulites of radiating fibers |
|  | quartzine | length slow fibers, fiber axis <00.1> crystal blades |
| Moganite |  |  |
| Opal | opal-CT | length slow fibers (lussatite) lepidospheres of platelets |
|  | opal-C | parallel platy {101} massy, tangled platy |

Further preferred inorganic micronized insoluble substances are talc:

The talc lattice is composed of infinite two-dimensional ($\frac{2}{\infty}$) silicate double layers $\{[Si_3O_5]^{2-}\}_3$ or $\frac{2}{\infty}[Si_4O_{10}]^{4-}$ in which the apical O atoms of all of the $SiO_4$ tetrahedral within one individual layer point in the same direction, and the OH groups occupy the centers of the hexagons formed by these apical oxygen atoms. The apical O atoms of all of the $SiO_4$ tetrahedral within an individual layer point in the same direction, and the OH groups occupy the centers of the hexagons formed by these apical oxygen atoms. Within a double layer, the apical O atoms and OH groups of one layer are in direct contact with the corresponding atoms of the other layer, forming octahedral voids. These voids are filled by positively charged magnesium ions, which compensate for the negative charges of the silicate. One magnesium ion is coordinated octahedrally by 4 O and 2 OH, the coordination number being symbolized by $Mg^{[6]}$.

Pyrophyllite:

The pyrophyllite structure contains an infinite coherent two-dimensional silicate double layer of linked $[SiO_4]$ tetrahedral: $\frac{2}{\infty}\{[Si_2O_5]^{2-}\}_2$ or $\frac{2}{\infty}[Si_4O_{10}]^{4-}$, in which all apical O atoms of the $SiO_4$ tetrahedra within one $[SiO_5]$ layer point in the same direction, and the OH groups occupy the centers of the hexagons formed by these oxygen atoms. In the double layer, the oxygen layers formed by the O atoms and OH groups are situated directly opposite each other, and they are linked together by $Al^{3+}$, which is octahedrally coordinated by 4 O and 2 OH. This coordination number is symbolized by $Al^{[6]}$. The resulting silicate double layer ("pyrophyllite layer") is therefore electrically neutral and is only weakly bonded to the neighbouring double layers by Van der Waals forces. This results in the laminar structure and pronounced cleavage of pyrophyllite in the direction (001). In talc, unlike pyrophyllite, the two single layers are bonded by $Mg^{2+}$ ("talc layer") instead of $Al^{3+}$. Thus, in pyrophyllite only ⅔ of the octahedral coordination centers are occupied by $Al^{[6]}$, while all ⅔ in talc are occupied by $Mg^{[6]}$.

Mica:

Micas are members of a class of silicates known as phyllo- or sheet silicates, a term which reflects their crystal structure. The general chemical formula for mica is $W(X, Y)_{2-3}Z_4O_{10}(OH, F)_2$, where W corresponds to K, Na, and Ca, or more rarely Ba, Rb, and Cs. The X, Y site is occupied by any two ions of Al, Mg, Fe, or Li, and less frequently of Mn, Cr, and Ti. Normally Z is Si or Al, but may also be Fe or Ti. As with other silicates the primary building unit of mica is the $SiO_4$ tetrahedron. The tetrahedra are linked together via their three basal oxygen ions to form a network of hexagonal cells with the apical oxygen ions all pointing in the same direction. The idealized basic structural unit of mica comprises two layers of tetrahedra in which the apical oxygen ions point toward each other. The voids between the bases of tetrahedra in adjacent layers and between adjacent apical oxygen ions provide the cation sites. The interapical plane is occupied by the octahedrally coordinated X, Y ions which may be any two of Al, Mg, Fe, or Li. The W sites (filled by K, Na, and less frequently Ca cations) are in 12-fold coordination with the basal oxygen ions. Most commonly these stacking sequences lead to either one- or two-layered monoclinic cells (denoted as 1 M and 2 $M_1$), an alternative two-layered monoclinic cell (2 $M_2$), or a three-layered trigonal unit (3 T).

Most important types of mica are listed in the table below:

ing rings to form zigzag bands (or "double crank-shaft chains") making use of three of the four common vertices. These bands are bonded in both the b and c direction by the fourth common oxygen atom of each (Si, Al) atom to form three-dimensional tetrahedral frameworks. As a result, the (010) and (001) planes are rather weakly bonded and readily cleaved. This property is characteristic of all feldspars. The cations $K^+$, $Na^+$, and $Ca^{2+}$, and more rarely $Sr^{2+}$ and $Ba^{2+}$, occupy the large spaces within the framework of tetrahedra, and are coordinated to oxygen in a fairly irregular manner.

Nepheline and Related Compounds:

The alkali aluminosilicate nepheline, $KNa_3[AlSiO_4]_4$, a feldspathoid, belongs to the nepheline group of tectosilicates without nontetrahedral anions. The aluminum:silicon ratio is 1:1. Structure and Mineralogy. As in all tectosilicates, the oxygen ions at the vertices of the $[AlO_4]$ and $[SiO_4]$ tetrahedra in nepheline are linked to the four neighbouring tetrahedra. This produces a three-dimensional open framework in which the relatively large $Na^+$ and $K^+$ cations are located in the spaces between the tetrahedra. In tectosilicates, these spaces can be occupied by alkaline-earth ions, nontetrahedral anions (e.g., in the feldspathoids sodalite and scapolite), or water (in zeolites). In minerals of the nepheline group the tetrahedra exhibit a hexagonal or pseudohexagonal arrangement. In nepheline, alternating $[AlO_4]$ and $[SiO_4]$ tetrahedra are linked together at common vertices to form an easily distorted high-tridymite structure with six-membered rings. The apices of the $[AlO_4]$ tetrahedra point parallel to the c axis, and those of the $[SiO_4]$ tetrahedra point in the opposite direction.

| Name | CAS registry number | Formula |
|---|---|---|
| Muscovite | [99401-63-5] | $K_2Al_4[Si_6Al_2O_{20}](OH, F)_4$ |
| Biotite | [112593-95-0] | $K_2(Mg, Fe^{2+})_{6-4}(Fe^{3+}, Al, Ti)_{0-2}[Si_{6-5}Al_{2-3}O_{20}] (OH, F)_4$ |
| Phlogopite | [110710-26-4] | $K_2(Mg, Fe^{2+})_6[Si_6Al_2O_{20}] (OH, F)_4$ |
| Lepidolite | [114705-28-1] | $K_2(Li, Al)_{5-6}[Si_{6-7}Al_{2-1}O_{20}] (OH, F)_4 3 K(Li, Al)_{2.5-3.0}[Si_{3-3.5}Al_{1-0.5}O_{10}] (OH, F)_2$ |
| Zinnwaldite | [116813-68-4] | $K_2(Fe_{2-1}^{2+}, Li_{2-3}Al_2) [Si_{6-7}Al_{2-1}O_{20}] (OH)_4$ |
| Paragonite | [106495-33-4] | $Na_2Al_4[Si_6Al_2O_{20}] (OH)_4$ |
| Glauconite | [102785-61-5] | $(K, Na, Ca)_{1.2-2.0}(Fe^{3+}, Al, Fe^{2+}, Mg)_{4.0}[Si_{7-7.6}Al_{1-0.4}O_{20}] (OH)_4 \cdot n (H_2O)$ |
| Margarite | [1318-86-1] | $Ca_2Al_4[Si_4Al_4O_{20}] (OH)_4$ |
| Clintonite, xan-thophyllite | [12199-34-7] | $Ca_2(Mg, Fe)_{4.6}Al_{1.4}[Si_{2.5}Al_{5.5}O_{20}] (OH)_4$ |

Bentonite:

Smectite is the name for a group of sodium, calcium, magnesium, iron, lithium aluminum silicates, which include the individual minerals sodium montmorillonite, calcium montmorillonite, nontronite, saponite, and hectorite. The rock in which these smectite minerals are usually dominant is bentonite.

Feldspar:

Feldspars [68476-25-5] are anhydrous alkali/alkaline-earth aluminosilicates that closely resemble each other in structure and properties. The feldspars are tectosilicates. The $[(Si, Al)O_4]$ tetrahedra are linked at all four vertices yielding a framework $[Si_{4-x}Al_xO_8]^{x-}$. The voids within the tetrahedral framework contain alkali metal or alkaline-earth ions for charge compensation. The structure is composed of four-membered rings, $[(Si, Al)_4O_{12}]$, containing $(AlSi_3)$ or $(Al_2Si_2)$ in each ring. The rings are linked by common oxygen atoms (two on each side) in the a direction to two neighbour- Unlike the high-tridymite structure, $Si^{4+}$ ions in nepheline are replaced by $Al^{3+}$ ions in half of the tetrahedral positions. In order to maintain charge neutrality, 3 $Na^+$ ions and 1 $K^+$ ion are found per formula unit in the centers of the channels parallel to the c axis.

Leucite:

The potassium aluminum silicate leucite, a feldspathoid, belongs to the analcime—leucite group of tectosilicates without nontetrahedral anions. The aluminum:silicon ratio is 1:2. Structure and Mineralogy. As with all the tectosilicates, the oxygen ions at the vertices of the $[AlO_4]$ and $[SiO_4]$ tetrahedra are linked to four neighbouring tetrahedra. This produces a three-dimensional open framework in which $K^+$ ions are located in the spaces within the framework. Whereas in the nepheline group the arrangement of tetrahedra is hexagonal or pseudohexagonal, the minerals of the analcime—leucite group have a cubic or pseudocubic arrangement.

Leucite [001302-34-7], K[AlSi$_2$O$_6$], is dimorphous. Below 605° C., it exists as low leucite and above 605° C. as high leucite Olivine:

Olivine (peridot, chrysolite) [1317-71-1] is a rock-forming nesosilicate (an orthosilicate, i.e., a silicate with isolated [SiO$_4$]$^{4-}$ tetrahedra hold together by metallic ions) belonging to the olivine series of minerals (Mg, Fe)$_2$[SiO$_4$]. There is an infinite series of solid solutions of the end members forsterite (Fo) [015118-03-3], Mg$_2$[SiO$_4$], and fayalite (Fa), Fe$_2$[SiO$_4$], The intermediate members are olivine (Mg$_{90-70}$, Fe$_{10-30}$)$_2$[SiO$_4$], hyalosiderite (Mg$_{70-50}$, Fe$_{30-50}$)$_2$[SiO$_4$], hortonolite (Mg$_{50-30}$, Fe$_{50-70}$)$_2$[SiO$_4$], and ferrohortonolite (Mg$_{30-10}$, Fe$_{70-90}$)$_2$[SiO$_4$]. Other members of the olivine series include tephroite Mn$_2$[SiO$_4$], knebelite, (Mn, Fe)$_2$[SiO$_4$], and iron knebelite (Fe, Mn)$_2$[SiO$_4$].

Andalusite:

Andalusite [12183-86-1] belongs to the nesosubsilicates (orthosilicates that contain isolated [SiO$_4$] tetrahedra and additional nontetrahedral anions), and, like kyanite (Section Kyanite and sillimanite (Section Sillimantite), is a mineral of the Al$_2$SiO$_5$ group. Structure and Mineralogy. Al$_2$SiO$_5$ can form three different crystal structures, i.e., Al$_2$SiO$_5$ exhibits polymorphism in the form of andalusite, sillimanite and kyanite. In all three phases one aluminum atom always has the coordination number six, i.e., it is surrounded octahedrally by six oxygen ions. The [Al$_I$O$_6$] octahedra are linked by common edges to form chains parallel to the c axis. The c$_0$ dimension in all three minerals is therefore approximately the same (ca. 0.55 nm). The other aluminum atom in andalusite has the coordination number five, in sillimanite four, and in kyanite six. The chains of octahedra in andalusite are held together by [AlO$_5$] and [SiO$_4$] groups. In andalusite none of the bonds break preferentially, so that andalusite has a higher Mohs hardness (7½) than sillimanite or kyanite. Libethenite Cu$_2$[OH/PO$_4$], adamine Zn$_2$[OH/AsO$_4$] and eveite Mn$_2$[OH/AsO$_4$] are isotypical with andalusite.

Kyanite:

Kyanite [1302-76-7] (cyanite, disthene) belongs to the nesosubsilicates (orthosilicates that contain isolated [SiO$_4$] tetrahedra and additional nontetrahedral anions) and, like andalusite (Section Andalusite) and sillimanite (Section Sillimanite), is a mineral of the Al$_2$SiO$_5$ group. Structure and Mineralogy. One aluminum atom always has the coordination number six, the [Al$_I$O$_6$] octahedra being linked by common edges to form chains parallel to the c axis. The other aluminum atom in kyanite also has the coordination number six. The chains of [Al$_I$O$_6$] octahedra are joined to other [Al$_{II}$O$_6$] octahedra, which are attached alternately to the right and left and are also linked via isolated [SiO$_4$] tetrahedra to form stable planar structures parallel to [100]. Vacant octahedra form open channels parallel to (001).

Sillimanite:

Sillimanite (fibrolite) belongs to the nesosubsilicates (orthosilicates that contain isolated [SiO$_4$] tetrahedra and additional nontetrahedral anions) and, like andalusite (Section Andalusite), kyanite (Section Kyanite) and mullite, is a mineral of the Al$_2$SiO$_5$ group. Structure and Mineralogy. One aluminum atom always has the coordination number six. The [Al$_I$O$_6$] octahedra are linked by common edges to form chains parallel to the c axis. The other aluminum atom in sillimanite has the coordination number four. The chains of octahedra in sillimanite are laterally bonded by [Al$_{II}$O$_4$] and isolated [SiO$_4$] tetrahedra which form bands of [Al$_2$Si$_2$O$_{10}$] tetrahedra from two linked chains of [AlSiO$_6$]. The four-coordinated aluminum in sillimanite cannot be substituted by silicon. Parallel to b (010), very strongly bonded layers are formed from the [AlO$_6$] chains and [Al$_2$Si$_2$O$_6$] bands. These can easily be cleaved from the neighbouring layers by separation at the apices of the [AlO$_6$] octahedra. This explains the perfect cleavage of sillimanite parallel to {010}. The chain structure also accounts for the generally fibrous structure of sillimanite crystals (fibrolite). As sillimanite has chains of tetrahedra, it is classified as an inosilicate (chain silicates, i.e., silicates with infinite chains of [SiO$_4$]$^{4-}$ tetrahedra).

Mullite

Mullite [1302-93-8] belongs to the nesosubsilicates (orthosilicates that contain isolated [SiO$_4$] tetrahedra and additional nontetrahedral anions) and is very similar to sillimanite (Section Sillimanite) in its structure and properties. Structure and Mineralogy. Mullite has a sillimanite structure, but differs from sillimanite in having a deficiency of oxygen. Since some of the silicon atoms in the [SiO$_4$] tetrahedra are replaced by Al$^{3+}$, some of the positions normally occupied by oxygen atoms are left unoccupied to maintain charge balance. Therefore, mullite has a higher aluminum content than sillimanite and has a chemical composition between 3 Al$_2$O$_3$.2 SiO$_2$ and 2 Al$_2$O$_3$.SiO$_2$.

Vermiculite:

Vermiculite belongs to the phyllosilicates (sheet or layer silicates) and has a mica-like foliated structure. It displays the typical properties of the montmorillonite—saponite group to a pronounced degree: the layers have a greater excess charge and a greater capacity for cation exchange than talc or pyrophyllite layers. The structure contains layers similar to those found in talc, pyrophyllite, biotite, and muscovite. It comprises infinite, two-dimensional double silicate layers $\triangleq$ [Si$_4$O$_{10}$]$^{4-}$. Part of the Si$^{4+}$ is substituted by Al$^{3+}$, and the terminal oxygen ions of the [(Si, Al)O$_4$] tetrahedra are always on the same side. The hexagons formed by these oxygen ions have hydroxyl groups at their centers. In this double layer, the oxygen layers formed from O (bound to one Si) and OH groups face each other directly, forming octahedral voids. These voids are occupied mainly by Mg$^{2+}$, but also by Fe$^{3+}$ and Al$^{3+}$, which hold together the two Si$_2$O$_5$/OH sheets. The octahedral voids are formed by four oxygen atoms and two hydroxyl groups. Due to the partial replacement of Si$^{4+}$ by Al$^{3+}$, the double layer pocket Mg$_3$[(SiAl)$_4$O$_{10}$/(OH)$_2$] has a slight excess negative charge, which is compensated by additional cations, e.g., Mg. These cations, together with water molecules, are interlayered between the layer pockets, usually Mg$^{2+}$ or, less frequently, Ca$^{2+}$. This interlayer (intermediate layer) has a positive excess charge and consists of a double layer of H$_2$O—Mg$^{2+}$—H$_2$O, in which the H$_2$O locations may be only partially occupied. Each H$_2$O in this interlayer is linked to an oxygen atom in the neighbouring silicate double layer by a hydrogen bond. Thus, vermiculite structurally resembles a kind of talc expanded by H$_2$O that has been formed from (hydrous) mica by potassium depletion.

Perlite:

Perlite of rhyolitic composition is a natural, volcanic glass that is usually black or gray, but sometimes brownish red. It has curved shrinkage cracks and therefore breaks up into spheroidal granules. It is usually produced by rapid cooling of rhyolitic melts (rhyolite being the volcanic equivalent of granite). Being a volcanic glass, perlite contains few crystals and only a small amount of water (2-6% combined water). Naturally-occurring glasses containing 3-8% water are known as pitchstone (hydrated glass).

Pumice:

Pumice [001332-09-8] is not a crystalline silicate mineral, but a light-colored, highly vesiculated, foamed volcanic glass of mainly acid character (>66% $SiO_2$, rhyolite), with a high melt viscosity, high pore volume (>50%) and variable water content.

Wollastonite:

Wollastonite [013983-17-0], $Ca_3[Si_3O_9]$, is polymorphic. Three modifications occur naturally, the commonest being low wollastonite which has two polytypical structural modifications: triclinic wollastonite (–1T) and monoclinic wollastonite (–2M, parawollastonite). In monoclinic wollastonite, the $[SiO_4]$ tetrahedra are linked to form infinite one-dimensional dreier single chains of $[Si_3O_9]^{6-}$ units. These are bonded together by $Ca^{2+}$ ions (which balance the electrical charge), and the chains lie parallel to b [010]. This explains why the crystals are always extended in the direction of b [010]. The monoclinic structure is derived from the triclinic by "inner twinning" on the (100) plane. Wollastonite (–1T) and wollastonite (–2M) are therefore inosilicates (silicates containing $[SiO_4]$ tetrahedra in infinite chains).

Further examples for micronized insoluble substances which can be used according to the present invention are birefringent nanocomposites, birefringent glitter particles as described in U.S. Pat. No. 6,475,609, birefringent materials as described in WO0121678, U.S. Pat. No. 4,461,886, EP1134270, anisotropic organic compounds as described in WO9216519, birefringent polymer particles as described in: Mikhailov, N. V.; Maiboroda, V. I.; Nikolaeva, S. S. Kolloidnyi Zhurnal (1959), 21 246-7., WO2004024778; Meeten, G. H.; Navard, P. Dep. Phys., City London Polytech., London, UK. Journal of Polymer Science, Polymer Physics Edition (1984), 22(12), 2159-63; Nichols, Mark E.; Robertson, Richard E. Dep. Mater. Sci. Eng., Univ. Michigan, Ann Arbor, Mich., USA. Journal of Polymer Science, Part B: Polymer Physics (1994), 32(3), 573-7.

Furthermore, starch and chemically modified starches can be used as micronized insoluble substances according to the present invention, like *Zea Mays* (Amidon De Mais MST (Wackherr), Argo Brand Corn Starch (Corn Products), Pure-Dent (Grain Processing), Purity 21 C (National Starch)), rice starch (D.S.A. 7 (Agrana Stärke), Oryzapearl (Ichimaru Pharcos)); distarch Phosphate (Corn PO4 (Agrana Stärke); corn PO4 (Tri-K)); sodium corn starch octenylsuccinate (C* EmCap—Instant 12639 (Cerestar USA)); aluminium starch octenylsuccinate (Covafluid AMD (Wackherr), Dry Flo-PC (National Starch), Dry Flo Pure (National Starch), Fluidamid DF 12 (Roquette)); textile fibers and cellulose-particles.

Preferably polymer microparticles like hollow polymer microparticles, porous polymer microparticles, like polyethylene-particles, polypropylene-particles, polyamide-particles, polyacrylonitrile-particles, polyester-particles, polymethylmethacrylate particles and polyurethane particles can be use as micronized insoluble particles.

The insoluble or sparingly soluble micronized substances used in the present cosmetic or dermatological composition can be used as single substances or as mixtures of more than one, for example 2, 3 or 4 single components.

The insoluble substances, which are preferably used in the micronised state, may be prepared according to any known process suitable for the preparation of microparticles, for example wet-milling, wet-kneading spray-drying, by the expansion according to the RESS process or by reprecipitation from suitable solvents.

The micronised particles so obtained usually have an average particle size from 0.02 to 10 micrometer, preferably from 0.03 to 5 micrometer and more especially from 0.05 to 3 micrometer.

Cosmetic UV absorbers are substances, which significantly reduce the transmission of UV light when applied on human skin. Typical is an SPF value higher than 4 if the cosmetic formulation contains at least 5% of such a cosmetic UV absorber.

As cosmetic UV filters which are soluble in the oil phase of the cosmetic composition especially non-micronised compounds are preferred, i.e. organic UV absorbers selected from the class of the p-aminobenzoic acid derivatives, salicylic acid derivatives, benzophenone derivatives, dibenzoylmethane derivatives, diphenyl acrylate derivatives, benzofuran derivatives, polymeric UV absorbers, comprising one or more organosilicon radicals, cinnamic acid derivatives, camphor derivatives, trianilino-s-triazine derivatives, s-triazine derivatives, phenylbenzimidazolesulfonic acid and salts thereof, menthyl anthranilates and benzotriazole derivatives.

Preferably, the following UV filters are of special interest: aminobenzophenone derivatives of formula

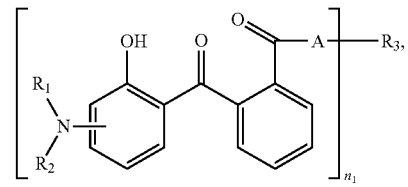

wherein $R_1$ and $R_2$ independently from each other are; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;

$n_1$ is a number from 1 to 4;

when $n_1$=1, $R_3$ is a saturated or unsaturated heterocyclic radical; hydroxy-$C_1$-$C_5$alkyl; cyclohexyl optionally substituted with one or more $C_1$-$C_5$alkyl; phenyl optionally substituted with a heterocyclic radical, aminocarbonyl or $C_1$-$C_5$alkylcarboxy;

when $n_1$ is 2, $R_3$ is an alkylene-, cycloalkylene, alkenylene or phenylene radical which is optionally substituted by a carbonyl- or carboxy group; a radical of formula *—$CH_2$—C≡C—$CH_2$—* or $R_3$ together with A forms a bivalent radical of the formula (1a)

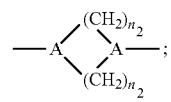

wherein
n$_2$ is a number from 1 to 3;
when n$_1$ is 3,
R$_3$ is an alkanetriyl radical;
if n$_1$ is 4,
R$_3$ is an alkanetetrayl radical;
A is —O—; or —N(R$_5$)—; and
R$_5$ is hydrogen; C$_1$-C$_5$alkyl; or hydroxy-C$_1$-C$_5$alkyl.
aminobenzophenone derivatives of the formula

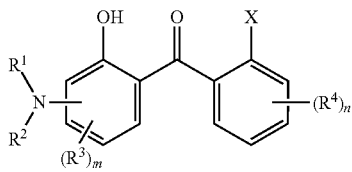

wherein
R$^1$, R$^2$ independently from each other is hydrogen, C$_1$-C$_{20}$alkyl; C$_2$-C$_{20}$alkenyl; C$_3$-C$_{10}$cycloalkenyl; wherein R$^1$ and R$^2$ may form a five- or six-membered ring;
R$^3$, R$^4$ independently from each other is C$_1$-C$_{20}$alkyl; C$_2$-C$_{20}$alkenyl; C$_3$-C$_{10}$ cycloalkenyl, C$_1$-C$_{20}$alkoxy, C$_1$-C$_{20}$alkoxycarbonyl, C$_1$-C$_{20}$alkylamino, di(C$_1$-C$_{20}$alkyl)amino, optionally substituted aryl or Heteroaryl;
X is hydrogen; COOR$^5$; CONR$^6$R$^7$;
R$^5$, R$^6$, R$^7$ independently from each other is hydrogen, C$_1$-C$_{20}$alkyl; C$_2$-C$_{20}$alkenyl; C$_3$-C$_{10}$cycloalkyl; C$_3$-C$_{10}$cycloalkenyl; (Y—O)$_q$-Z; optionally substituted aryl;
Y is —(CH$_2$)$_2$—; —(CH$_2$)$_3$—; —(CH$_2$)$_4$—; —CH(CH$_3$)—CH$_2$—;
Z is —CH$_2$—CH$_3$; —CH$_2$—CH$_2$—CH$_3$; —CH$_2$—CH$_2$—CH$_2$—CH$_3$; CH(CH$_3$)—CH$_3$;
m is 0; 1; 2; or *;
n is 0; 1; 2; 3; or 4; and
Q is a number from 1 to 20.
the compound of formula

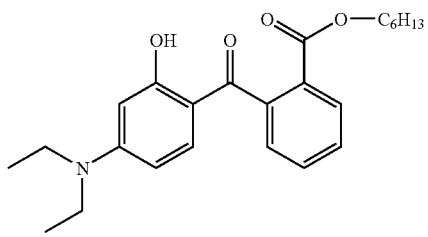

compound of formula

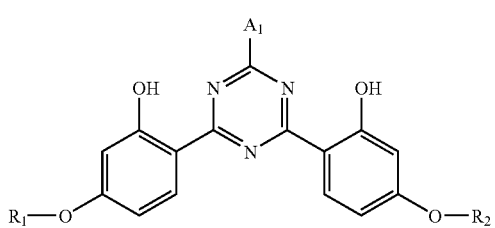

in which
R$_1$ and R$_2$, independently of one another, are C$_3$-C$_{18}$alkyl; C$_2$-C$_{18}$alkenyl; a radical of the formula —CH$_2$—CH(—OH)—CH$_2$—O-T$_1$; or
R$_1$ and R$_2$ are a radical of the formula

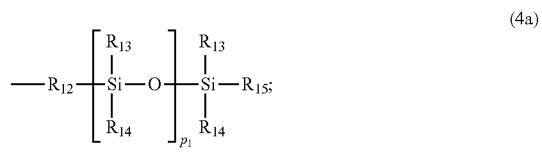

(4a)

R$_{12}$ is a direct bond; a straight-chain or branched C$_1$-C$_4$alkylene radical or a radical of the formula —C$_{m_1}$H$_{2m_1}$— or —C$_{m_1}$H$_{2m_1}$—O—;
R$_{13}$, R$_{14}$ and R$_{15}$, independently of one another, are C$_1$-C$_{18}$alkyl; C$_1$-C$_{18}$alkoxy or a radical of the formula

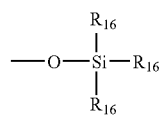

R$_{16}$ is C$_1$-C$_5$alkyl;
m$_1$ and m$_3$, independently of one another, are 1 to 4;
p$_1$ is 0 or a number from 1 to 5;
A$_1$ is a radical of the formula

(1b)

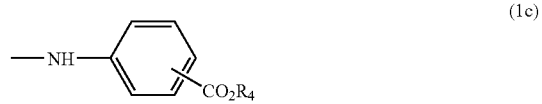

(1c)

or of the formula

(1d)

R$_3$ is hydrogen; C$_1$-C$_{10}$alkyl, —(CH$_2$CHR$_5$—O)$_{n_1}$—R$_4$; or a radical of the formula —CH$_2$—CH(—OH)—CH$_2$—O-T$_1$;

| | |
|---|---|
| R$_4$ | is hydrogen; M; C$_1$-C$_5$alkyl; or a radical of the formula —(CH$_2$)$_{m_2}$—O-T$_1$; |
| R$_5$ | is hydrogen; or methyl; |
| T$_1$ | is hydrogen; or C$_1$-C$_8$alkyl; |
| Q$_1$ | C$_1$-C$_{18}$alkyl; |
| M | is a metal cation; |
| m$_2$ | is 1 to 4; and |
| n$_1$ | is 1-16. | hydroxyphenyltriazine compound of formula

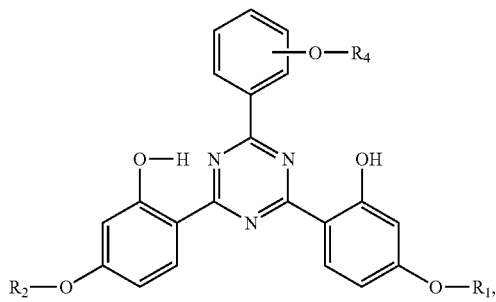

(e₂1)

wherein
R₁ and R₂ are each independently of the others C₁-C₁₈alkyl; C₂-C₁₀alkenyl; or phenyl-C₁-C₄alkyl; R₄ is hydrogen; or C₁-C₅alkyl.
dibenzoylmethane derivative of formula

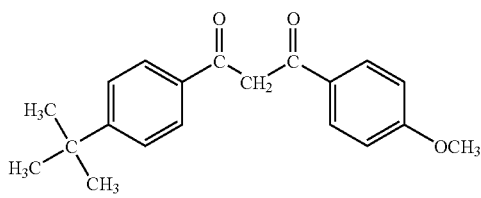

or

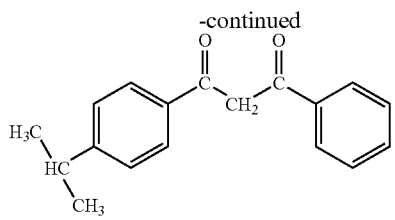

disodium phenyl dibenzimidazole tetrasulfonate (Heliopan AP).

benzoxazole-substituted triazine of the formula

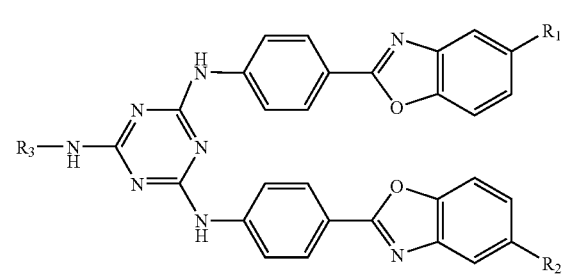

wherein
R₁, R₂ and R₃ independently from each other are branched or unbranched C₁-C₁₂alkyl.

Most preferably the UV absorber, if present in the oil phase are listed in the Table 1 below:

TABLE 1

| UV absorber present in the oil phase | | |
|---|---|---|
| No. | Chemical Name | CAS No. |
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxyphenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |

TABLE 1-continued

UV absorber present in the oil phase

| No. | Chemical Name | CAS No. |
|---|---|---|
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexylester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |

If an organic UV filter is present in the water-phase it is selected from the compounds listed in Table 2.

TABLE 2

UV absorber present in the water-phase

| No. | Chemical Name | CAS No. |
|---|---|---|
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]-propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mo-no sodium salt or Disodium phenyl dibenzimidazole tetrasulfonate or Neoheliopan AP | 349580-12-7, |

Preferably used in the present cosmetic dermatological composition of the present invention are the combinations of
organic UV absorber present in the oil phase and selected from triazine compounds of formula ($e_2$1) and melamin derivatives;
organic UV absorber present in the oil phase and selected from triazine compounds of formula ($e_2$1) and $CaCo_3$ (cacite);
organic UV absorber present in the oil phase and selected from triazine compounds of formula ($e_2$1) and $CaMgCO_3$ (dolomite).

The following combinations of micronized, insoluble particles and organic UV absorbers, soluble in the water or in the oil phase are preferred:

| UV absorber (A) | Bifringent micronized particle (B) | |
|---|---|---|
| 1-[4-(1,1-dimethylethyl)phenyl]-3-(4-methoxyphenyl)propane-1,3-dione | Micronized Melamine 0.1-5% | Micronized Carbonate or Sulfate of Ca, Sr, Ba 0.1-5% |
| 2-Ethylhexyl 2-cyano,3,3-diphenyl-acrylate | Micronized Melamine 1-10% | Micronized Carbonate or Sulfate of Ca, Sr, Ba 1-10% |

-continued

| UV absorber (A) | Bifringent micronized particle (B) | |
| --- | --- | --- |
| 2-ethylhexyl 4-methoxycinnamate | Micronized Melamine 1-10% | Micronized Carbonate or Sulfate of Ca, Sr, Ba 0-10% |
| 2,4-bis{[4-(2-ethylhexyloxy)-2-hydroxy]phenyl}-6-(4-methoxyphenyl)-(1,3,5)-triazine | Micronized Melamine 1-5% | Micronized Carbonate or Sulfate of Ca, Sr, Ba 0-5% |
| Benzoic acid, 2-[4-(diethylamino)-2-hydroxybenzoyl]-, hexyl ester | Micronized Carbonate or Sulfate of Ca, Sr, Ba. 1-5% | Micronized Carbonate or Sulfate of Ca, Sr, Ba 0-5% |

A further aspect of the present invention is a cosmetic or dermatological composition comprising
(a) a micronized, insoluble or sparingly solulble substance which is not a cosmetic UV absorber having a refraction index of n=1 to 2.5 and a Δn=0.001 to 0.8 n;
(b) a UV-Filter which can be formulated in the oil- or water-phase;
(c) a water phase,
(d) an oil phase,
and a cosmetically acceptable carrier.

Preferably, the cosmetic or dermatological composition comprises as component (a), a micronized, insoluble substance which has a particle size of 0.01 to 5 μm and the average refractive index of this particle (n[parallel]+n[perpendicular]/2) differs not more than 0.3 from the refractive index of the oil phase in which the particle is dispersed.

Preferably, the concentration of the micronized, insoluble substance (a) is >0.5% of the cosmetic composition, more preferably >1%, and most preferably >2%.

The LSF- and/or SPF factor indicates the prolongation of the exposure to the sun of an individual, which is enabled by the use of the sun protective agent. It is the quotient of erythema threshold time with sun protective agent and erythema threshold time without sun protective agent.

The cosmetic or dermatological compositions are preferably used as boosters for UV-absorbance of cosmetic sunscreen formulations.

A measure for the UV protection determination in the sense of the present invention is for example the light protecting factor (LSF and/or SPF (=SunProofFactor)) or also IPD values.

The composition of the present invention may be obtained as follows:

The insoluble or sparingly soluble birefringent substance (dispersed phase) is slurred in water or in cosmetically acceptable oil and optionally mixed with an emulsifying agent or a surfactant as dispersing agent.

If water is used as continuous phase the dispersion may also be stabilized with an electrolyte.

Using a cosmetic oil as continuous phase the oil-soluble UV absorber can be added, or, in case of a liquid UV absorber the dispersion process can be carried out directly in the liquid UV absorber as continuous phase (for example octyl methoxy cinnamate).

The mixture is kneadable if it is high-viscous and grindable if it is low-viscous, depending from the moiety of the continuous phase.

The grindable slurry is grinded in a ball mill until the dispersion has a particle size from 0.03 to 10 μm, preferably from 0.03 to 5 μm, and most preferably from 0.03 to 3 μm.

If the continuous phase of this dispersion is aqueous it can be placed into the aqueous phase of a cosmetic or dermatological preparation; an oily continuous phase leads to an admixture into the oil- or fatty- or wax-phase.

In a preferred embodiment of the present invention the oil-soluble UV absorber is dissolved and mixed with the non-micronized insoluble non UV-absorbing substance, or both components are mixed and the micronization is carried out in the oil phase.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned micronizable insoluble substance and the oil-soluble UV filter, the cosmetic or pharmaceutical preparations may contain further adjuvants like fatty alcohols, fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers super-fatting agents, surfactants, consistency regulators/thickeners and rheology modifiers, polymers, biogenic active ingredients, deodorising active ingredients, anti-dandruff agents, antioxidants, hydrotropic agents, preservatives and Bacteria-inhibiting agents, bacteria-inhibiting agents, perfume oils, colourants or polymeric beads or hollow spheres as SPF enhancers.

Cosmetic or Pharmaceutical Preparations

Cosmetic or pharmaceutical formulations are contained in a wide variety of cosmetic preparations. There come into consideration, for example, skin-care preparations, -bath preparations, cosmetic personal care preparations, foot-care preparations, light-protective preparations, skin-tanning preparations, insect-repellents, deodorants, antiperspirants, preparations for cleansing and caring for blemished skin, hair-removal preparations in chemical form (depilation), having preparations, fragrance preparations or cosmetic hair-treatment preparations, Presentation Forms The final formulations listed may exist in a wide variety of presentation forms, for example:
 in the form of liquid preparations as a W/O, O/W, O/W/O, W/O/W or PIT emulsion and all kinds of microemulsions,
 in the form of a gel,
 in the form of an oil, a cream, milk or lotion,
 in the form of a powder, a lacquer, a tablet or make-up,
 in the form of a stick,
 in the form of a spray (spray with propellent gas or pump-action spray) or an aerosol,
 in the form of a foam, or
 in the form of a paste.

The cosmetic preparation according to the invention is distinguished by excellent protection of human skin against the damaging effect of sunlight.

EXAMPLES

Example 1

General Dispersion Formulations (in Oil)

A dispersion is prepared comprising the following components:

| | |
|---|---|
| (1a) birefringent particle | 40-60 parts |
| (1b) emulsifier (as disclosed in chapter "emulsifier") | 0-10 parts |
| (1c) dissolved UV filter | 01-20 parts |
| (1d) cosmetic oil according | 0-60 parts |

By simple adding the materials a slurry is obtained, which is micronized in a laboratory agitator ball mill. A very coarse-grained material (a) having a starting grain size of >0.5 μm must be precutted first, for example by milling in a corundum disk mill, a dissolver and/or a colloid mill or by kneading.

Also a dry grinding process may be used.

Examples 2-11

Preparation Examples for Dispersions in Oil (in % b.w)

| Dispersion number | Component | Ex 2 Disp 1o | Ex 3 Disp 2o | Ex 4 Disp 3o | Ex 5 Disp 4o | Ex 6 Disp 5o | Ex 7 Disp 6o | Ex 8 Disp 7o | Ex 9 Disp 8o | Ex 10 Disp 9o | Ex 11 Disp 10o |
|---|---|---|---|---|---|---|---|---|---|---|---|
| Melamine | (1a) | 55 | 40 | 0 | 0 | 0 | 50 | 0 | 0 | 0 | 0 |
| Phatalimide | (1a) | 0 | 0 | 40 | 0 | 0 | 0 | 0 | 0 | 0 | 0 |
| 5-Aminophtalic acid | (1a) | 0 | 0 | 0 | 40 | 0 | 0 | 0 | 0 | 0 | 0 |
| Montmorillonite Tonsil 414 FF (Süd-Chemie) | (1a) | 0 | 0 | 0 | 0 | 40 | 0 | 0 | 0 | 0 | 0 |
| Compound of formula (101) | (1a) | 0 | 0 | 0 | 0 | 0 | 0 | 40 | 40 | 40 | 40 |
| Polystearylglyceride-PEG 30 | (1b) | 5 | 10 | 10 | 10 | 10 | 0 | 10 | 10 | 10 | 10 |
| Dehymuls PGHS | (1b) | 0 | 0 | 0 | 0 | 0 | 0 | 0 | 0 | 0 | 0 |
| Compound of formula (102) | (1c) | 0 | 0 | 0 | 0 | 0 | 0 | 0 | 5 | 0 | 0 |
| Compound of formula (103) | (1c) | 0 | 0 | 0 | 0 | 0 | 0 | 0 | 0 | 5 | 0 |
| DHHB | (1c) | | | | | | 0 | | | | 10 |
| BEMT | (1c) | 0 | 10 | 10 | 10 | 10 | 10 | 0 | 0 | 0 | 0 |
| Cyprylic/Capric Triglyceride | (1d) | 40 | 0 | 0 | 0 | 0 | 40 | 0 | 0 | 0 | 0 |
| C12-C15 Alkyl benzoate | (1d) | 0 | 40 | 40 | 40 | 40 | 0 | 50 | 45 | 45 | 40 |

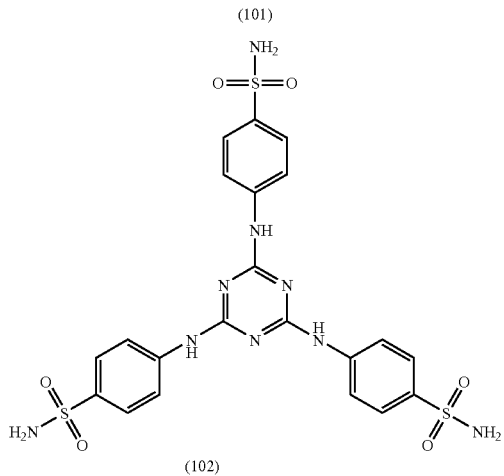

(101)

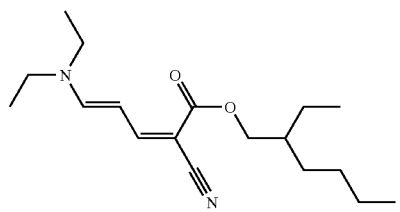

(102)

| Dispersion number | Component | Ex 2 Disp 1o | Ex 3 Disp 2o | Ex 4 Disp 3o | Ex 5 Disp 4o | Ex 6 Disp 5o | Ex 7 Disp 6o | Ex 8 Disp 7o | Ex 9 Disp 8o | Ex 10 Disp 9o | Ex 11 Disp 10o |
|---|---|---|---|---|---|---|---|---|---|---|---|

(103)

[Chemical structure diagram]

Examples 12 to 17

Dispersions in Water (Electrolyte Stabilized, in % b.w.)

A dispersion is prepared comprising the following components:

| | | | |
|---|---|---|---|
| (2a) | birefringent particle | 40-60 | parts |
| (2b) | Electrolyte | 0.1-10 | parts |
| (2c) | water | 30-60 | parts |
| (1d) | dissolved UV filter | 0.1-20 | parts |

| Dispersion number | Component | Disp 1w (Ex. 12) | Disp 2w (Ex. 13) | Disp 3w (Ex. 14) | Disp 4w (Ex. 15) | Disp 5w (Ex. 16) | Disp 6w (Ex. 17) |
|---|---|---|---|---|---|---|---|
| Melamine | (2a) | 49 | 49 | 0 | 0 | 0 | 49 |
| Phatalimide | (2a) | 0 | 0 | 49 | 0 | 0 | 0 |
| 5-Aminophtalic Acid | (2a) | 0 | 0 | 0 | 49 | 0 | 0 |
| Monmorillonite Tonsil 414 FF (Süd-Chemie) | (2a) | 0 | 0 | 0 | 0 | 49 | 0 |
| Sodium chloride | (2b) | 1 | 0 | 1 | 1 | 1 | 0 |
| Magnesiumchloride | (2b) | 0 | 0 | 0 | 0 | 0 | 1 |
| Potassium sulfate | (2b) | 0 | 1 | 0 | 0 | 0 | 0 |
| Phenylbenzimidazol sulfonic acid | (2d) | 9 | 10 | 10 | 10 | 10 | 10 |
| water, deion. | (2c) | 40 | 40 | 40 | 40 | 40 | 40 |

Example 18

Preparation of a Cosmetic Formulation Comprising Dispersion 1 (in the Oil Phase)

| | Trade Name | INCI name | % b.w |
|---|---|---|---|
| Part A | Axol C62 | Glyceryl Stearate Citrate | 1.5 |
| | Disp 1o | Melamine in miglyol 812 N (55%) | 10.0 |
| | Cetiol OE | Dicaprylyl Ether | 3.00 |
| | Eutanol G | Octyl dodecanol | 2.0 |
| | Lanette 18 | Stearyl Alcohol | 1.5 |
| | Softisan 100 | Hydrogenated Cocoglycerides | 1.0 |
| | Tinosorb OMC | Ethylhexyl Methoxycinnamate | 2.0 |
| | Tinosorb S | 2,4-bis{[4-(2-ethylhexyloxy)-2-hydroxy]-phenyl}-6-(4-methoxyphenyl)-(1,3,5)-triazine | 1.7 |
| | Neo Heliopan | Octocrylene | 1.1 |
| | Antaron V-216 | PVP/Hexadecene Copolymer | 1.3 |
| Part B | Pemulen TR-2 | Acrylates/C10-30 Alkyl Acrylate crosspolymer | 0.15 |
| | Water | Aqua | qs to 100 |
| | Rhodicare S | Xanthan Gum | 0.15 |
| | Disodium EDTA | Disodium EDTA | 0.1 |
| | Glycerine | Glycerine | 4 |
| Part C | Germaben II | Diazolidinyl Urea/Methyl paraben/Propyl paraben/Propylene Glycol | 0.70 |
| Part D | NaOH ad 10% | Sodium Hydroxide | qs |

Manufacturing Instruction:

Phase A is prepared by incorporation of all the ingredients except Pemulen TR-2, then the mixture is stirred under moderate speed and heat up to 80° C.

At the latest stage of incorporation, Pemulen TR-2 is dispersed into the oil-phase. The phase B is heated up to 75-80° C.

Phase A is poured into phase B under increase of stirring.

The mixture is homogenized for 15 seconds at 10 000 rpm.

At approximately 70° C. Pemulen TR-2 is neutralized with NaOH solution.

Under 45° C. phase D is added, then pH is adjusted to about 6-7.

Sunscreen: in-vitro SPF=27; In Vivo SPF=23.

Example 19

Preparation of a Cosmetic Formulation Comprising Dispersion 1 (in the Water-phase)

|  | Trade name | INCI-Name | % w/w (as supplied) |
|---|---|---|---|
| Part A | Axol C62 | Glyceryl Stearate Citrate | 1.5 |
|  | Miglyol 8810 | Butyle Glycol Dicaprylate/DiCaprate | 6.0 |
|  | Cetiol OE | Dicaprylyl Ether | 4.0 |
|  | Eutanol G | Octyl dodecanol | 2.5 |
|  | Lanette 18 | Stearyl Alcohol | 1.5 |
|  | Softisan 100 | Hydrogenated Cocoglycerides | 1.0 |
|  | Tinosorb OMC | Ethylhexyl Methoxycinnamate | 2.0 |
|  | BEMT | BEMT | 1.7 |
|  | Neo Heliopan | Octocrylene | 1.1 |
|  | Antaron V-216 | PVP/Hexadecene Copolymer | 1.3 |
|  | Pemulen TR-2 | Acrylates/C10-30 Alkyl Acrylate crosspolymer | 0.15 |
| Part B | Water | Aqua | qs to 100 |
|  | Disp 1w |  | 10.0 |
|  | Rhodicare S | Xanthan Gum | 0.15 |
|  | Disodium EDTA | Disodium EDTA | 0.1 |
|  | Glycerine | Glycerine | 4.0 |
| Part C | Germaben II | Diazolidinyl Urea/Methyl paraben/Propylparaben/Propylene Glycol | 0.70 |
| Part D | NaOH ad 10% | Sodium Hydroxide | qs |

Phase A is prepared by incorporation of all the ingredients, then the mixture is stirred under moderate speed and heated until 80° C.

At the latest incorporation, Pemulen TR-2 is dispersed into the oil-phase.

The phase B is heated at 75-80° C.

Phase A is poured into phase B under accelerated stirring.

The mixture is homogenized for 15 seconds at 10 000 rpm.

At approximately 70° C. Pemulen TR-2 is neutralized with NaOH solution.

Under 45° C. phase D is added, then the pH is adjusted to about 6-7.

Sunscreen In-vitro SPF=20

For determination of SPF/MPF values of the dispersions below the following formulation is prepared:

(a) 20 parts of one of the dispersions from Examples(19a)-(19h),
(b) 17 parts Capric/Caprylic Triglyceride,
(c) 5 parts Brij 72 (PEG-2-Stearate),
(d) 5 parts Eutanol G 16 (C-16 alkylalcohol),
(e) 3 parts glycerine, and
(f) 50 parts water, deion.

The components of the oil phase (a)-(d) are added together and warmed up to 75° C.

Under stirring the water phase (e) and (f) which is also warmed up to 75° C. is added and homogenized with a Ultra-Turrax (10,000 rpm).

The formulation so obtained is applied on sand blasted PMMA plates according to a process described by Wendel et al (Wendel et al., SÖFW-Journal, 127(11); 2001).

After that the MPF values and the SPF value are determined with an Optometrix-SPF-290.

Formulations having a particle content of 8% and a content of dissolved UV absorber of 2% are obtained.

TABLE 3

Determination of the SPF factor

|  | Birefringent particles | Dissolved UV-Absorber | SPF with particle | SPF without particle |
|---|---|---|---|---|
| Example 19a (a = Disp 3o from Ex. 2-11) | Phtalimide | BEMT | 14 (2% BEMT) | 6.5 (2% BEMT) |
| Example 19b (a = Disp 2o from Ex. 2-11) | Melamine | BEMT | 13.5 (2% BEMT) | 6.5 (2% BEMT) |
| Example 19c (a = Disp 5o from Ex. 2-11) | montmorillonite Tonsil 414 FF (Süd-Chemie) | BEMT | 12.6 (2% BEMT) | 6.5 (2% BEMT) |
| Example 19d (a = Disp 4o from Ex. 2-11) | 5-Aminoiso-phtalic acid | BEMT | 8 (2% BEMT) | 6.5 (2% BEMT) |
| Example 19e (a = Disp 7o from Ex. 2-11) | Compound of formula (101) | BEMT | 19 (2% BEMT) | 6.5 (2% BEMT) |
| Example 19f (a = Disp 8o from Ex. 2-11) | Compound of formula (101) | DHHB | 11 (1.6% DHHB) | 4.8 (1.6% DHHB) |

TABLE 3-continued

| | Birefringent particles | Dissolved UV-Absorber | SPF with particle | SPF without particle |
|---|---|---|---|---|
| Example 19g (a = Disp 9o from Ex. 2-11) | Compound of formula (101) | Compound of formula (103) | 9 (1.6% Compound of formula (103)) | 5.5 (1.6% Compound of formula (103)) |
| Example 19h (a = Disp 10o from Ex. 2-11) | Compound of formula (101) | Compound of formula (102) | 8 (1.6% Compound of formula (102)) | 6.5 (1.6% Compound of formula (102)) |

BEMT = Bis-Ethylhexyloxyphenol Methoxyphenyl Triazine
DHHB = Diethylamino Hydroxybenzoyl Hexyl Benzoate Results:

As can be seen from Table 3 the compositions of the present invention comprising a birefringent particle show a remarkable increase in SPF.

Example 20

Preparation of UV Absorber Dispersions Containing Micronized Calcium Salts

Dispersion 20a:

| 50 wt.-% | Calcite ($CaCO_3$) |
|---|---|
| 4 wt-% | Arlacel P135 (PEG-30-Polyhydroxy stearinic acid) |
| ad 100% | Miglyol 812N (Capric/Caprylic triglyceride) |

Dispersion 20b:

| 50 wt.-% | Calcite ($CaCO_3$) |
|---|---|
| 4 wt-% | Arlacel P135 (PEG-30-Polyhydroxy stearinic acid) |
| 10 wt.-% | Ethylhexyl methoxy cinnamate |
| 7.5 wt.-% | Bis-Ethylhexyloxyphenol Methoxyphenyl Triazine |
| ad 100% | Miglyol 812N (Capric/Caprylic triglyceride) |

Dispersion 20c:

| 50 wt-% | Calcite (CaCO3) |
|---|---|
| 4 wt-% | Arlacel P135 (PEG-30-Polyhydroxy stearinic acid) |
| 10 wt.-% | Ethylhexyl methoxy cinnamate |
| 7.5 wt.-% | Bis-Ethylhexyloxyphenol Methoxyphenyl Triazine |
| ad 100% | $C_{12}$-$C_{15}$ Alkylbenzoate |

Dispersion 20d:

| 50 wt.-% | Calcite ($CaCO_3$) |
|---|---|
| 4 wt-% | Arlacel P135 (PEG-30-Polyhydroxy stearinic acid) |
| 15 wt.-% | Octocrylene |
| 7.5 wt.-% | Bis-Ethylhexyloxyphenol Methoxyphenyl Triazine |
| ad 100% | Miglyol 812N (Capric/Caprylic triglyceride) |

Preparation Method:

The slurries of dispersion 20a-20d are homogenized using a high shear apparatus (Ultra-turrax) prior wet-milling with a bead mill, down to a particle size (calcite) of 0.5 to 5 μm. Such dispersions can be incorporated into cosmetic w/o or o/w emulsions.

Extinction Measurement:

For the extinction measurement a formulation using dispersion 20a is prepared by heating all components on 60° C. prior stirring and homogenizing using an ultra-turrax:

| 50% | dispersion 20a |
|---|---|
| 0.75% | Bis-Ethylhexyloxyphenol Methoxyphenyl Triazine |
| 49.25% | w/o emulsion a | w/o Emulsion a:

| Oil Phase: | |
|---|---|
| Paraffinum Liquidum | 12 |
| Cyclomethicone | 7 |
| Isohexadecane | 6 |
| Isopropyl Palmitate | 5 |
| Cera Microcristallina | 2 |
| PEG-40 Sorbitan Perisostearate | 1.8 |
| Polyglyceryl-3-Diisostearate | 1.7 |
| *Prunus Dulcis* | 0.7 |
| Tocopheryl Acetate | 0.5 |
| Lanolin Alcohol | 0.5 |
| Water Phase: | |
| Sodium Lactate | 1.1 |
| Lactic Acid | 1.0 |
| $MgSO_4$ | 0.8 |
| $NaHCO_3$ | 0.4 |
| Citric Acid | 0.2 |
| Iodopropynyl Butylcarbamate | 0.2 |
| Fragrance | 0.1 |
| Water | ad 100 |
| Glycerine | 8 |

Both phases are heated separately to 80° C. The oil phase is added to the water phase under stirring prior emulsification.

This emulsion is measured in a Perkin-Elmer UV-Vis-spectrometer using 8 μm cuvettes. The extinction measured for this formulation is E=1.2 at 340 nm, whereas the placebo without any calcite is E=0.65 at 340 nm.

SPF Measurements:

For SPF measurements the dispersions 20a-20d are incorporated in an analogous way into a commercially available w/o-lotion.

Basic formulation: X % dispersion Y ad 100% w/o emulsion a

These preparations are applied on transpore tape (2 μl/cm$^2$) and measured using an Optometrix-SPF 290S-analyzer.

Results (SPF Values) are listed in Table 4

TABLE 4

| SPF of dispersions containing micronized calcium salts | | | | |
|---|---|---|---|---|
| | X = 5 | X = 10 | X = 20 | X = 30 |
| Y = 16b | 2.7 | 5.3 | 13.7 | 25.3 |
| Placebo (y = 16b without Calcite) | 2.1 | 4.1 | 7.6 | 11.1 |
| Y = 16c | 3.1 | 5.5 | 14.5 | 28.1 |
| Y = 16d | — | 8.2 | 19 | 35 |

The invention claimed is:

1. A method for the enhancement of light protection of a cosmetic or dermatological composition, said method comprising dispersing insoluble or sparingly soluble micronized birefringent particles having an average refractive index of n=1 to 2.5 and a Δn=0.001 to 0.8 in an oil or water phase of a cosmetic or dermatological composition and the birefringent particles are selected from the group consisting of melamine polyphosphate, melamine cyanurate, melamine phosphate, melam (1,3,5-triazine-2,4,6-triamine-n-(4,6-diamino-1,3,5-triazine-2-yl) of the formula

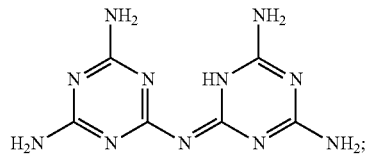

melem (-2,5,8-triamino 1,3,4,6,7,9,9b-heptaazaphenalene) of the formula

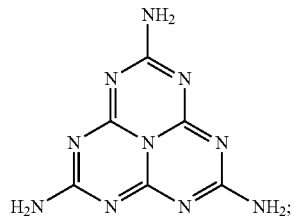 [SMILES: NC1=NC2=NC(N)=NC3=NC(N)=NC(=N1)N23]

melon (poly [8-amino-1,3,4,6,7,9,9b-heptaazaphenalene-2,5-diyl]imino) of the formula

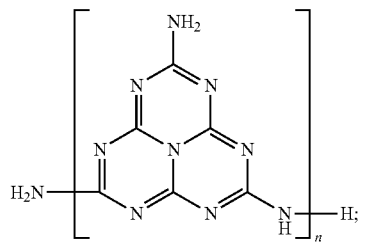

1,3,5-triazin-2(1H)-one, 4,6-diamino of the formula

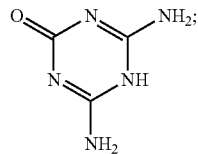

1,3,5-triazine-2,4(1H,3H)-dione, 6-amino- of the formula

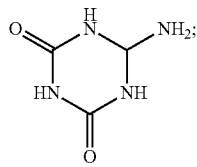

benzene-1,2,4,5-tetracarboxamide, biphenyl-4,4'-dicarboxamide, biphenyl-4-carboxylic amide,
isophthalamide and terephthalamide;
cyanuric acid, diphenyl urea, propylurea, 3-methyl-1,1-diphenylurea;
Isatin; 5-amino-isophthalic acid; diphenyl sulfone, and a triazine compound of the formula

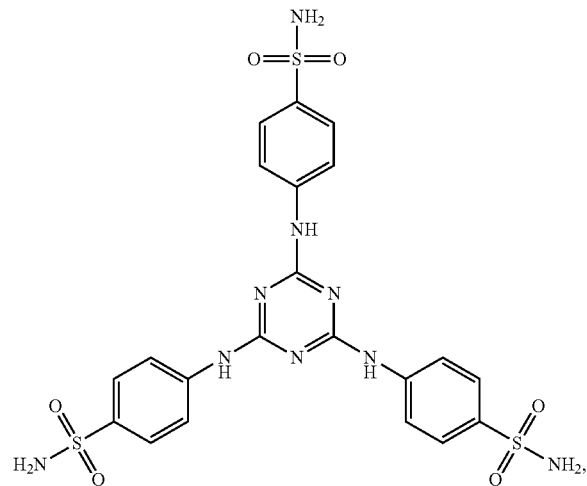 [SMILES: NS(=O)(=O)c1ccc(Nc2nc(Nc3ccc(S(N)(=O)=O)cc3)nc(Nc3ccc(S(N)(=O)=O)cc3)n2)cc1]

wherein the insoluble or sparingly soluble micronized birefringent particles have a particle size from 0.02 to 10 micrometers, and wherein said composition further comprises at least one cosmetic UV filter that is soluble in the water or oil phase.

2. A method according to claim 1, wherein the birefringent particles contain a hydrophobic or hydrophilic surface.

3. A method according to claim 1, wherein the birefringent particles are crystalline or semi-crystalline.

4. A method according to claim 1, wherein the birefringent particles are a high melting solid, wherein the high melting solid has a melting point of >80° C.

5. A method according to claim 1, wherein the oil phase comprises a UV filter selected from the group consisting of p-aminobenzoic acid derivatives, salicylic acid derivatives, benzophenone derivatives, dibenzoylmethane derivatives, diphenyl acrylate derivatives, benzofuran derivatives, polymeric UV absorbers comprising one or more organosilicon radicals, cinnamic acid derivatives, camphor derivatives, trianilino-s-triazine derivatives, s-triazine derivatives, phenylbenzimidazolesulfonic acid and salts thereof, menthyl anthranilates and benzotriazole derivatives.

6. A method according to claim 5, wherein the UV filter is selected from the group consisting of
(+/−)-1,7,7-trimethyl-3-[(4-methylpheny)methylenebicyclo[2.2.1]heptan-2-one; 1,7,7-trimethyl-3-(phenylmethylene)bicyclo[2.2.1]heptan-2-one; (2-hydroxy-4-methoxyphenyl)(4-methylphenyl)methanone; 2,4-dihydroxybenzophenone; 2,2',4,4'-tetrahydroxybenzophenone; 2-hydroxy-4-methoxy benzophenone; 2,2'-dihydroxy-4,4'-dimethoxybenzophenone; 2,2'-dihydroxy-4-methoxybenzophenone; 1-[4-(1,1-dimethylethyl)phenyl]-3-(4-methoxyphenyl)propane-1,3-dione; 3,3,5-trimethyl cyclohexyl-2-hydroxy benzoate; isopentyl p-methoxycinnamate; menthyl-o-aminobenzoate; menthyl salicylates; 2-ethylhexyl 2-cyano,3,3-diphenylacrylate; 2- ethylhexyl 4-(dimethylamino)benzoate; 2- ethylhexyl 4-methoxycinnamate; 2- ethylhexyl salicylates; benzoic acid, 4,4',4"-(1,3,5-triazine-2,4,6-triyltriimino)tris-, tris (2-ethylhexyl)ester; 2,4,6-trianilino-(p-carbo-2'-ethyl-hexyl-1'-oxi)-1,3,5-triazine; benzoic acid, 4-amino-, ethyl ester, polymer with oxirane; 2-propenamide, N-[[4-[(4,7,7-trimethyl-3-oxobicyclo[2.2.1]hept-2-ylidene)methyl]phenyl]methyl]-, homopolymers; triethanolamine salicylates; 2,2'-methylene-bis-[6-(2H-benzotriazol-2-yl)-4-(1,1,3,3-tetramethylbutyl)-phenol]; 2,4-bis{[4-(2-ethylhexyloxy)-2-hydroxyl-phenyl]-6-(4-methoxyphenyl)-(1,3,5)-triazine; benzoic acid, 4,4'-[[6-[[4-[[(1,1-dimethylethyl)aminolcarbonyl]phenyl]amino]1,3,5-triazine-2,4-diyl]diimino]bis-, bis (2-ethylhexyl)ester; phenol, 2-(2H-benzotriazol-2-yl)-4-methyl -6-[2-methyl-3-[1,3,3,3-tetramethyl-1-[(trimethylsilyl)oxyldisiloxanyl]propyl]-; dimethicodiethylbezalmalonate; benzoic acid, 2-[4-(diethylamino)-2-hydroxybenzoyl]-, hexyl ester; 1,3,5-triazine, 2,4,6-tris(4-methoxyphenyl)-; 1,3,5-triazine, 2,4, 6-tris[4-[(2-ethylhexyl)oxy]phenyl]-; 2-propenoic acid, 3-(1 H-imidazol-4-yl)-; benzoic acid, 2-hydroxy-, [4-(1-methylethyl)phenyl]methyl ester; 1,2,3-propanetriol, 1-(4-aminobenzoate); benzeneacetic acid, 3,4-dimethoxy-a-oxo-; 2-propenoic acid, 2-cyano-3,3-diphenyl-, ethyl ester; anthralinic acid, p-menth-3-yl ester; and 1,3,5-triazine-2,4,6-triamine, N,N'-bis[4-[5-(1,1-dimethylpropyl)-2-benzoxazolyl]phenyl]-N"-(2-ethylhexyl)-.

7. A method according to claim 1, wherein the water-phase comprises at least one UV filter selected from the group consisting of 2-hydroxy-4-methoxy benzophenone-5-sulfonic acid; alpha-(2-oxoborn-3-ylidene)toluene-4-sulphonic acid and its salts; methyl N,N,N-trimethyl-4-[(4,7,7-trimethyl-3-oxobicyclo[2,2,1]hept-2-ylidene)methyl]anilinium sulphate; 4-aminobenzoic acid; 2-phenyl-1H-benzimidazole-5-sulphonic acid; 3,3'-(1,4-phenylenedimethylene)bis[7,7-dimethyl-2-oxo-bicyclo [2.2.1]heptane-1-methanesulfonic acid]; 1H-benzimidazole-4,6-disulfonic acid, 2,2'-(1,4-phenylene)bis-, disodium salt; benzenesulfonic acid, 3-(2H-benzotriazol-2-yl)-4-hydroxy-5-(1-methylpropyl)-, monosodium salt; 1-dodecanaminium, N-[3-[[4-(dimethylamino)benzoyl]amino]propyl]N,N-dimethyl-, salt with 4-methylbenzenesulfonic acid (1:1); 1-propanaminium, N,N,N-trimethyl-3-[(1-oxo-3-phenyl-2-propenyl)amino]-, chloride; 1 H-benzimidazole-4,6-disulfonic acid, 2,2'-(1,4-phenylene)bis-; 1-propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt); and 2,2'-bis(1,4-phenylene)-1H-benzimidazole-4,6-disulphonic acid mono sodium salt and disodium phenyl dibenzimidazole tetrasulfonate.

8. A cosmetic or dermatological composition comprising:
(a) a water phase,
(b) an oil phase,
(c) a UV-Filter which can be formulated in the oil phase or in the water phase,
(d) insoluble or sparingly soluble micronized birefringent particles having an average refractive index of n=1 to 2.5 and a Δn=0.001 to 0.8 selected from the group consisting of melamine polyphosphate, melamine cyanurate, melamine phosphate, melam (1,3,5-triazine-2, 4,6-triamine-n-(4,6-diamino-1,3,5-triazine-2-yl) of the formula

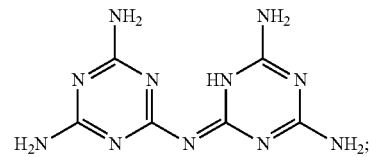 [SMILES: Nc1nc(N)nc(/N=c2/nc(N)nc(N)[nH]2)n1]

melem (-2,5,8-triamino 1,3,4,6,7,9,9b-heptaazaphenalene) of the formula

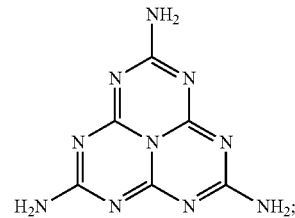

melon (poly[8-amino-1,3,4,6,7,9,9b-heptaazaphenalene-2,5-diyl]imino) of the formula

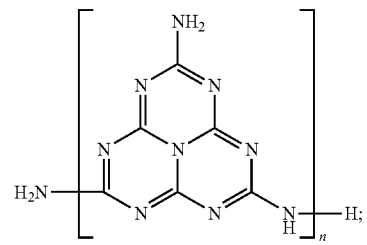

1,3,5-triazin-2(1H)-one, 4,6-diamino of the formula

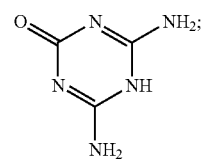

1,3,5-triazine-2,4(1H,3H)-dione, 6-amino- of the formula

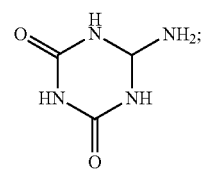

benzene-1,2,4,5-tetracarboxamide, biphenyl-4,4'-dicarboxamide, biphenyl-4-carboxylic amide, isophthalamide and terephthalamide;
cyanuric acid, diphenyl urea, propylurea, 3-methyl-1,1-diphenylurea;

Isatin; 5-amino-isophthalic acid; diphenyl sulfone, and a triazine compound of the formula

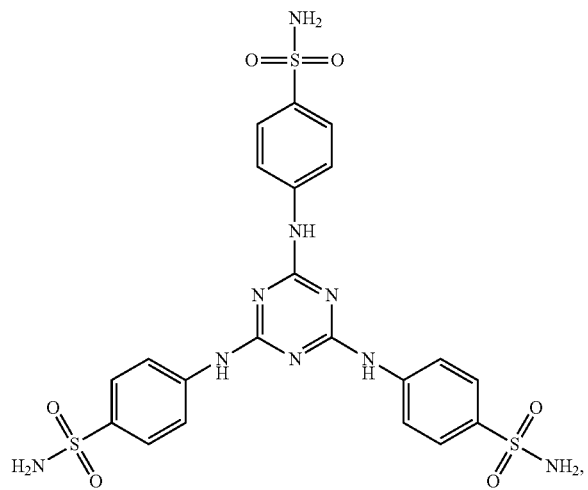 [SMILES: NS(=O)(=O)c1ccc(Nc2nc(Nc3ccc(S(N)(=O)=O)cc3)nc(Nc3ccc(S(N)(=O)=O)cc3)n2)cc1]

and a cosmetically acceptable carrier, wherein the insoluble or sparingly soluble micronized birefringent particles have a particle size from 0.01 to 5 micrometers and are dispersed in the oil phase or in the water phase.

9. A cosmetic composition according to claim 8, wherein the average refractive index of the particles (d) (n[parallel]+n[perpendicular]/2) differs not more than 0.3 from the refractive index of the oil phase in which the particles are dispersed.

10. A cosmetic composition according to claim 8, wherein the concentration of the particles (a) is >0.5%.

11. A cosmetic composition according to claim 8, wherein the concentration of the particles (a) is >1%.

12. A cosmetic composition according to claim 8, wherein the concentration of the particles (a) is >2%.

* * * * *